(12) United States Patent
Loescher

(10) Patent No.: US 7,228,859 B2
(45) Date of Patent: Jun. 12, 2007

(54) PRESSURE VENTING CIRCUIT FOR RESPIRATORY HUMIDIFICATION APPARATUS

(75) Inventor: Thomas C. Loescher, Rancho Santa Fe, CA (US)

(73) Assignee: Teleflex Medical Incorporated, Limerick, PA (US)

( * ) Notice: Subject to any disclaimer, the term of this patent is extended or adjusted under 35 U.S.C. 154(b) by 422 days.

(21) Appl. No.: 10/881,944

(22) Filed: Jun. 29, 2004

(65) Prior Publication Data

US 2005/0284475 A1    Dec. 29, 2005

(51) Int. Cl.
| | |
|---|---|
| A61M 15/00 | (2006.01) |
| A61M 16/10 | (2006.01) |
| A61M 15/08 | (2006.01) |
| B01D 19/00 | (2006.01) |
| B01D 14/00 | (2006.01) |
| B01D 53/14 | (2006.01) |
| B65D 83/00 | (2006.01) |

(52) U.S. Cl. .......................... 128/203.12; 128/203.16; 128/203.24; 96/155; 96/263; 222/397

(58) Field of Classification Search ........... 128/203.12, 128/203.25, 204.13, 204.14, 203.16, 203.26, 128/203.17; 261/42, 64.1, 72.1, 119.1; 165/111, 165/112, 110; 222/397, 394, 396; 96/155, 96/263
See application file for complete search history.

(56) References Cited

U.S. PATENT DOCUMENTS

| | | | |
|---|---|---|---|
| 4,110,419 A | 8/1978 | Miller | 261/142 |
| 4,172,105 A | 10/1979 | Miller et al. | 261/66 |
| 4,178,334 A * | 12/1979 | Miller | 261/142 |
| 4,366,105 A | 12/1982 | Nowacki | 261/35 |
| 4,500,480 A | 2/1985 | Cambio, Jr. | 261/104 |
| 4,674,494 A | 6/1987 | Wiencek | 128/203.16 |
| 4,765,327 A * | 8/1988 | Shim | 128/204.13 |
| 6,050,552 A | 4/2000 | Loescher et al. | 261/129 |
| 6,202,991 B1* | 3/2001 | Coniglio et al. | 261/121.1 |
| 6,988,497 B2* | 1/2006 | Levine | 128/203.27 |
| 2006/0151624 A1* | 7/2006 | Grundler et al. | 237/67 |

FOREIGN PATENT DOCUMENTS

GB    002126102 A  *  8/1982

* cited by examiner

*Primary Examiner*—Justine R. Yu
*Assistant Examiner*—K C Matter
(74) *Attorney, Agent, or Firm*—Baker & Hostetler LLP

(57) ABSTRACT

An improved humidifier assembly includes a tubing and a one-way valve for equalizing pressure between gas space of a water supply container and gas space of a humidifier vessel.

15 Claims, 5 Drawing Sheets

PRESSURE VENTING CIRCUIT FOR RESPIRATORY HUMIDIFICATION APPARATUS

BACKGROUND OF THE INVENTION

Humidifying apparatus such as disclosed in U.S. Pat. Nos. 4,110,419, 4,172,105, 4,366,105, 4,500,480, 4,674,494, 4,765,327 and 6,050,552 describe different variations of cartridge-type humidification systems and apparatus incorporating a heated humidifier module connected via tubing to a water supply reservoir. In these systems, the humidification chamber is installed within a heater receptacle. As water is evaporated in the heated humidification chamber replacement water is fed to the cavity from the adjacent water supply reservoir. The descriptions of the aforesaid patents are incorporated herein by reference.

In U.S. Pat. Nos. 4,500,480 and 6,050,552, a water level sensing tube positioned in the humidification chamber communicates with the air space above the water level in the water supply reservoir via tubing with a one-way valve. Water is fed to the humidification chamber from the bottom of the reservoir via tubing, also provided with a one-way valve. During continuous gas flow, for example, where the humidification apparatus is used with a CPAP system or is connected to a respirator or ventilator which directs respiratory gas into the humidification chamber under pressure, the pressure in the water supply reservoir equals the pressure to which the humidification chamber is exposed. Under certain conditions, the humidification cartridge may be exposed to pressures of 150 cm $H_2O$ or more during continuous gas flow, or pressures in excess of 120 cm $H_2O$ during intermittent gas flow. The high pressure is transferred ultimately to the reservoir via the one-way tube so that the pressure inside the reservoir is near or equal to the mean pressure to which the humidification chamber is exposed. During typical operation, such high pressures in the containers of the system are not problematic. However, sudden pressure reduction in the humidification chamber can result in rapid transfer of water from the reservoir and flooding of the chamber and even into the respiratory gas tubing to a patient. The apparatus described herein is designed to substantially reduce or eliminate such flooding.

SUMMARY OF THE INVENTION

The apparatus disclosed herein provides for transfer of fluid (gas) from the water supply reservoir to the humidification chamber to equalize pressure differential between the humidification chamber and the reservoir. More specifically, the apparatus functions to allow pressure gas in the space above water level in a water supply container to be directed to the space above water level in a humidifier vessel. In a preferred embodiment, the pressure equalizing apparatus comprises tubing communicating the air space above the water level in both the humidification chamber and the water reservoir, and a one-way valve in or cooperating with the tubing allowing fluid flow in the tubing from the water reservoir to the humidification chamber.

The invention includes a method for equalization of pressure differential, the humidifier chamber and water supply reservoir. More specifically, the method provides for delivering higher pressure in the water supply reservoir by venting the high pressure gas to the air space in the humidification chamber. Means for carrying out the method include piping and valving between the air spaces in the water supply reservoir and the humidifier vessel.

DETAILED DESCRIPTION OF THE PREFERRED EMBODIMENT

Figure 1:
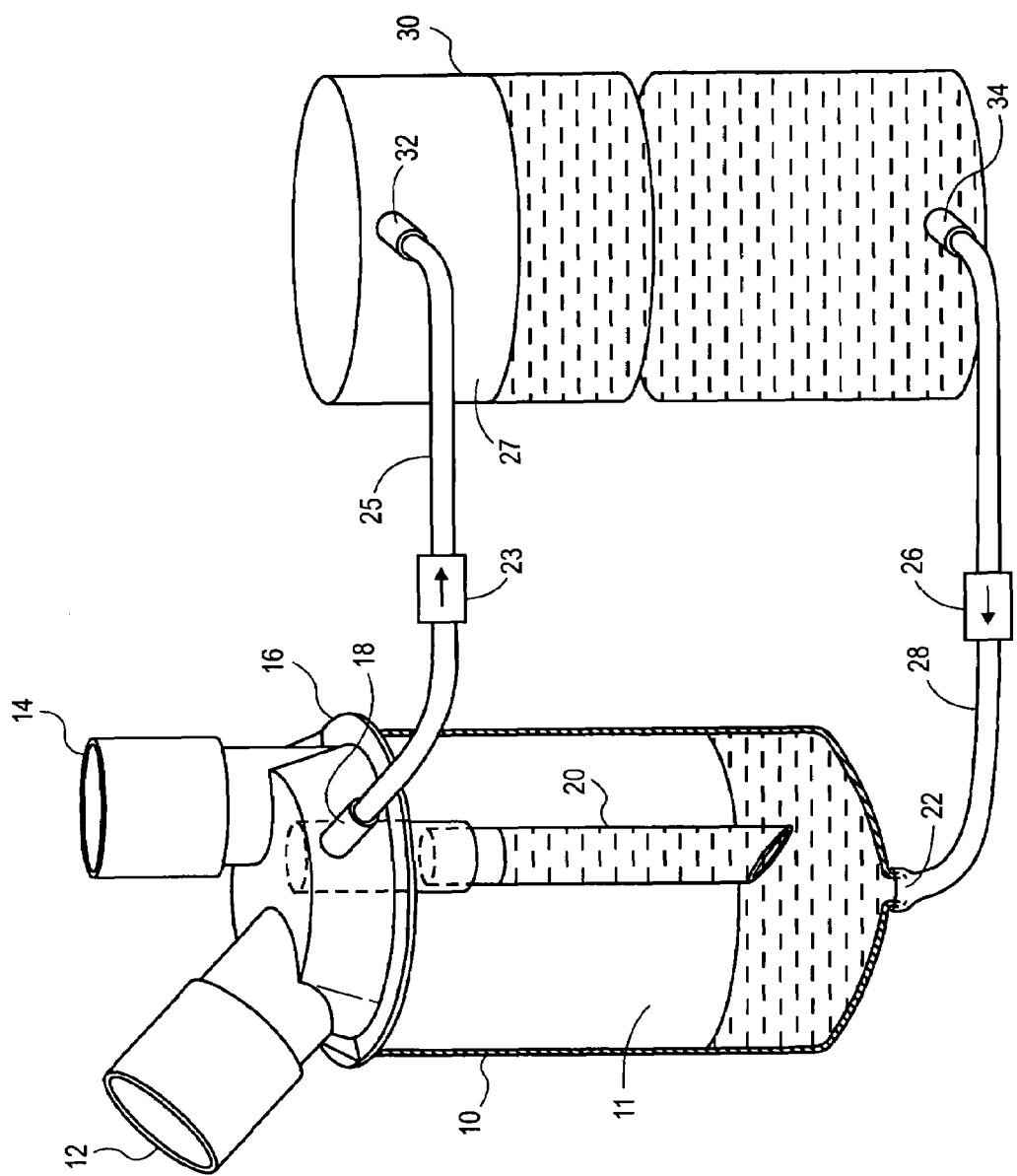
FIG. 1 illustrates a prior art humidifier assembly including a water supply reservoir, a humidifier vessel including a humidification chamber, and tubing and one-way valves communicating the humidifier vessel and water supply reservoir.

In FIG. 1, a prior art humidifier assembly is shown. The assembly includes a hollow humidifier vessel 10 with a water holding cavity 11, the vessel having a lid or cap 16 for enclosing the cavity. The cap is provided with a respiratory gas outlet 12, respiratory gas inlet 14 and a water level control port 18 communicating exteriorly of the humidifier vessel through a tubing adapter formed thereon. The respiratory gas inlet 14 is for receiving gas through suitable gas delivery tubing (not shown) from a respirator, and the outlet 12 secured to respiratory tubing (not shown) for directing humidified gas from the humidifier vessel to a patient, typically through a face mask, nose mask, tracheotomy mask or the like. The humidifier vessel 10 is also provided with a water level control pipe 20, the upper end of which is attached to an adapter extending from or communicating with water level control port 18. At the bottom or lower end of the humidifier vessel is a nipple or adapter 22 for directing water to the cavity.

The humidifier assembly also includes a water supply container and reservoir 30 having a port 32 adjacent to the upper end or top of the reservoir and communicating with the interior space of the reservoir, above the water level. Adjacent to the bottom end of the reservoir 30 is a port 34. Water from the reservoir is supplied via tubing 28, one end which is attached to port 34 on the reservoir 30 and the other end to water inlet nipple 22 of the humidifier vessel. The water supply tubing 28 is provided with a check valve or one-way valve 26 which allows water to be directed from the reservoir 30 to the humidifying vessel 10. Tubing 25 adjacent to the upper portion of the assembly is secured to port 32 on the water reservoir 30 and to water level control port 18 on the cap 16 of the humidifier vessel 10. Tubing 25 is also provided with a check valve or one-way valve 23 which allows fluid to pass from the humidifier vessel to the water reservoir. Further description and operation of the apparatus shown in FIG. 1 is described, for example, in U.S. Pat. No. 4,500,480.

Figure 2:
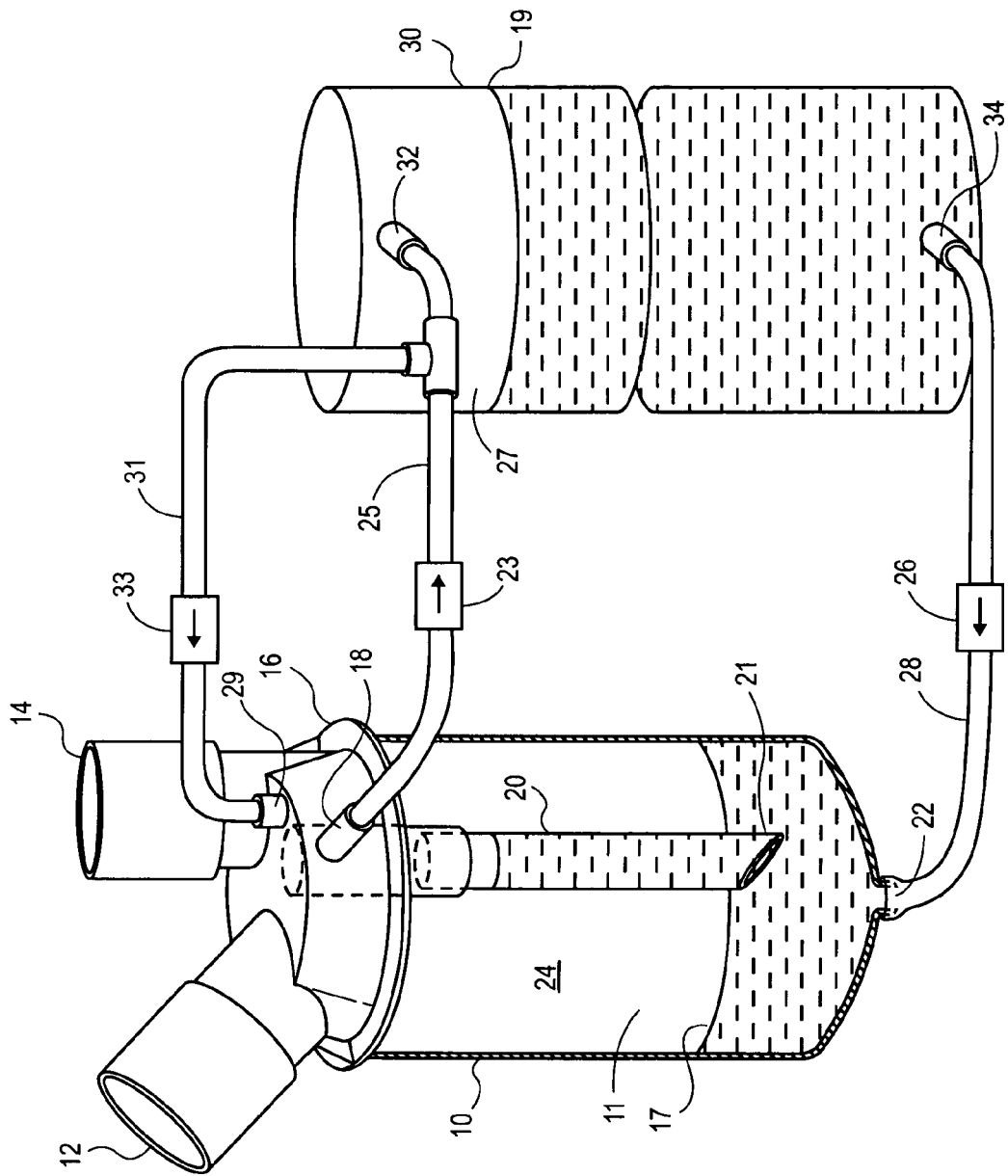
FIG. 2 illustrates an embodiment of a pressure equalizing apparatus of the invention installed in a humidifier assembly of FIG. 1.

Observing also FIG. 2, a preferred embodiment of the present invention comprises a pressure equalizing assembly or apparatus. In the preferred embodiment shown, such apparatus includes tubing 31 which communicates the interior cavity of humidifier vessel 10 with the interior cavity of water supply reservoir 30. One end of tubing 31 is secured to pressure vent port 29 on humidifier vessel cap 16. The other end of tubing 31 is secured to a flow splitting device shown as a tee adapter 35 along tubing 25. Tubing 31 is also provided with a check valve or one-way valve 33 whereby fluid may pass only from reservoir 30 to the humidifier vessel 10. It will also be observed that the tubing 31 communicates with port 32 above water level 19 in the water reservoir, and above water level 17 in humidifier vessel 10. Thus, the pressure equalizing assembly communicates with air space 27 in reservoir 30 and air space 24 in humidifier vessel 10. Although both one-way valves 23 and 33 are shown in FIG. 2 as located along tubing 25 and 31, respectively, either or both of these one-way valves may be located in the tubing adapters or in tee adapter 35. For example, one-way valve 23 may be located in the tubing adapter of water level control port 18 or tee adapter 35 and/or one-way valve 33 located in the tubing adapter of gas pressure vent port 29 or tee adapter 35.

In operation of the humidifier assembly shown in FIGS. 1 and 2, water from reservoir 30 is supplied via tubing 28 from the bottom of the reservoir at outlet port 34 to the bottom of water holding cavity 11 in humidifier vessel 10 through nipple 22 at the bottom of the vessel. One-way valve 26 prevents water from returning to the reservoir 30 from the humidifier vessel 10. As relatively dry respiratory gas is introduced into the humidifier vessel, it contacts heated water in the water holding cavity 11 and is humidified. The humidified gas is then directed via respiratory gas outlet 12 to a patient. As the water within the humidifier vessel evaporates, the water level is lowered, and the water level is sensed by water level control pipe 20, the bottom end 21 of which contacts and is submerged in the water. One end of tubing 25, communicates with the reservoir space 27 above the water level 19, and the other end with the water level control pipe 20 via water level control port 18. Thus, the water level control pipe maintains a substantially constant liquid level in the humidification chamber, whereby the water level in pipe 20 is the same as the water level in reservoir 30.

During operation of the apparatus which is connected to a ventilator, pressure in the humidifier vessel increases relative to the reservoir 30 as previously discussed. This relatively high pressure in the humidifier vessel is transferred to the reservoir via tubing 25 and one-way valve 23 whereby the water level in pipe 20 equalizes the pressure between the two containers. Thus, during continuous gas flow through the humidifier vessel, the pressure in the reservoir is equalized with the pressure within the humidifier vessel. When pressure in the humidifying vessel is suddenly changed, for example, when the pressurized vessel is disconnected from a respirator, the pressure in the water holding cavity is suddenly exposed to atmospheric pressure creating a substantial pressure gradient between the humidification chamber and the reservoir. In the prior art apparatus illustrated in FIG. 1, when such a pressure gradient is suddenly created, water is rapidly transferred through tubing 28 via one-way valve 26 until equilibrium is reached between the humidification chamber and the reservoir. Such equilibrium can result in excessive amounts of water from the reservoir flooding the humidification chamber which may also undesirably cause delivery of such water to the patient from the humidifying vessel via respiratory outlet 12.

Undesirable flooding of the humidifier vessel is prevented by the apparatus illustrated in FIG. 2. A substantial reduction in pressure in the humidifier vessel as described above will be equalized via tubing 31 and one-way valve 33 as pressure is equalized in space 24 in the humidifier vessel and space 27 in the reservoir 30, without substantial movement of water from the reservoir to the humidifier vessel in response to such pressure reduction. Communication of space 27 in reservoir 30 and space 24 in humidifier vessel 10 via tubing 31 allows transfer of gas from the reservoir to the humidification chamber above the water level also avoiding creation of aerosols or other particulate water from being delivered to a patient in response to any substantial pressure reduction within vessel 10. Such a configuration allows the reservoir to vent gas back to the humidification chamber without transfer of substantial fluid through the tubing 28 and one-way valve 26 when the pressure in the humidification chamber is substantially reduced.

Figure 3:
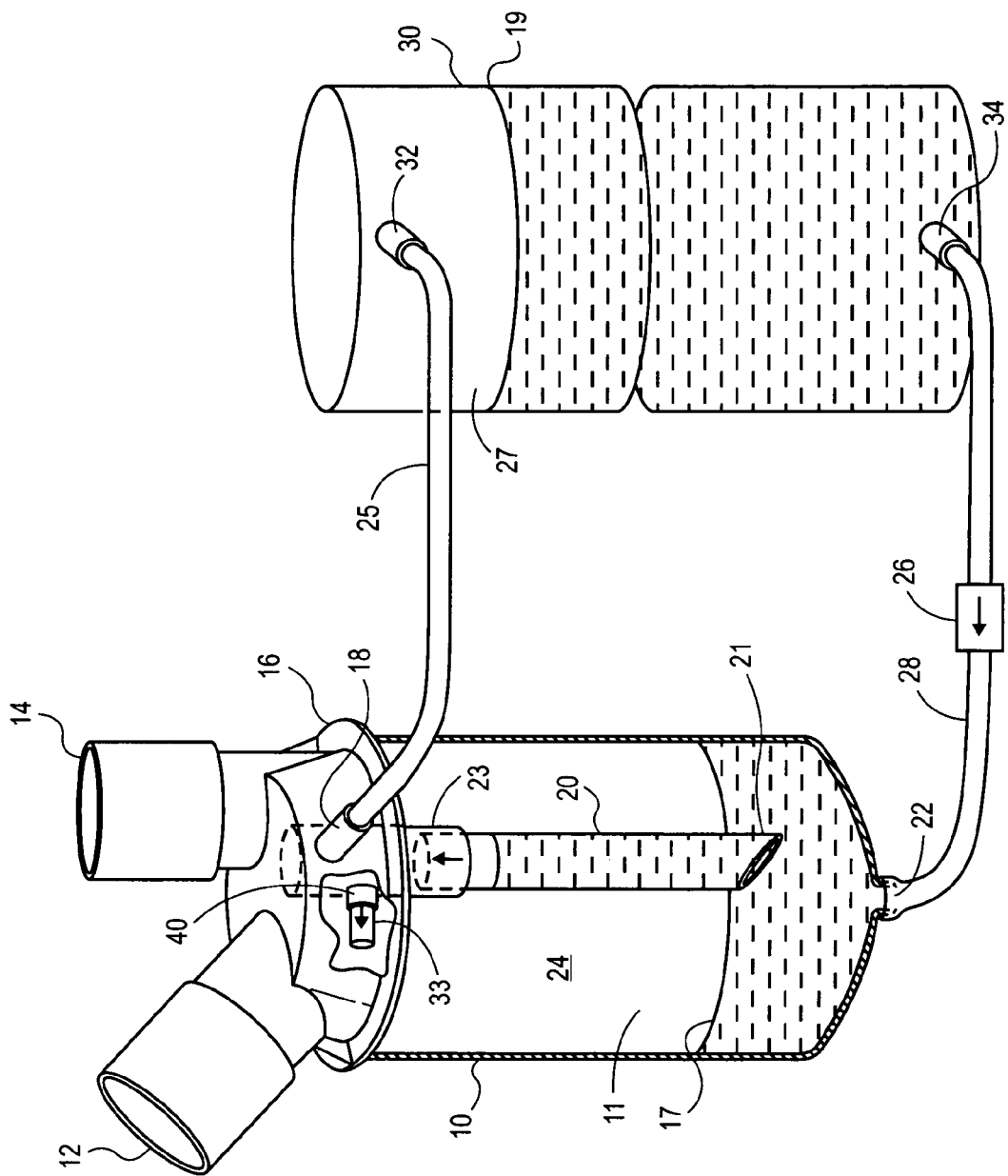
FIG. 3 illustrates another embodiment of a pressure equalizing apparatus with the valving installed within the humidifier vessel.

FIG. 3 illustrates another preferred embodiment in which the pressure equalizing valves are located inside the humidifier vessel. In the embodiment shown, a first check valve or one-way valve 23 is located in the water level control pipe 20 and a second check valve or one-way valve 33 is located in an inlet vent port pipe 40. These one-way valves 23 and 33 allow gas to flow only through the valve in the direction of the arrows illustrated. It will be observed that both of these valves operatively communicate with water level control port 18 which extends from cover or lid 16 of the humidifier vessel 10. Interior piping, tubing or adapters are formed on the underside of lid 16 to provide communication of the one-way valves and inlet vent port pipe 40 and water level control pipe 20 with the water level control port. An advantage of the embodiment shown in FIG. 3 is that only a single tube 25 is used for equalizing pressures in the water supply container 30 and humidifier vessel 10. The embodiment of FIG. 3 provides pressure equalization between the air space 27 in reservoir 30 with the air space 24 in humidifier vessel 10 via the single tubing 25. Thus, transfer of gas from the reservoir to the humidification chamber above the water level via vent port pipe 40 and one-way valve 33 is provided through the same tubing as used for the water level control via water level control pipe 20 as previously described.

Figure 4:
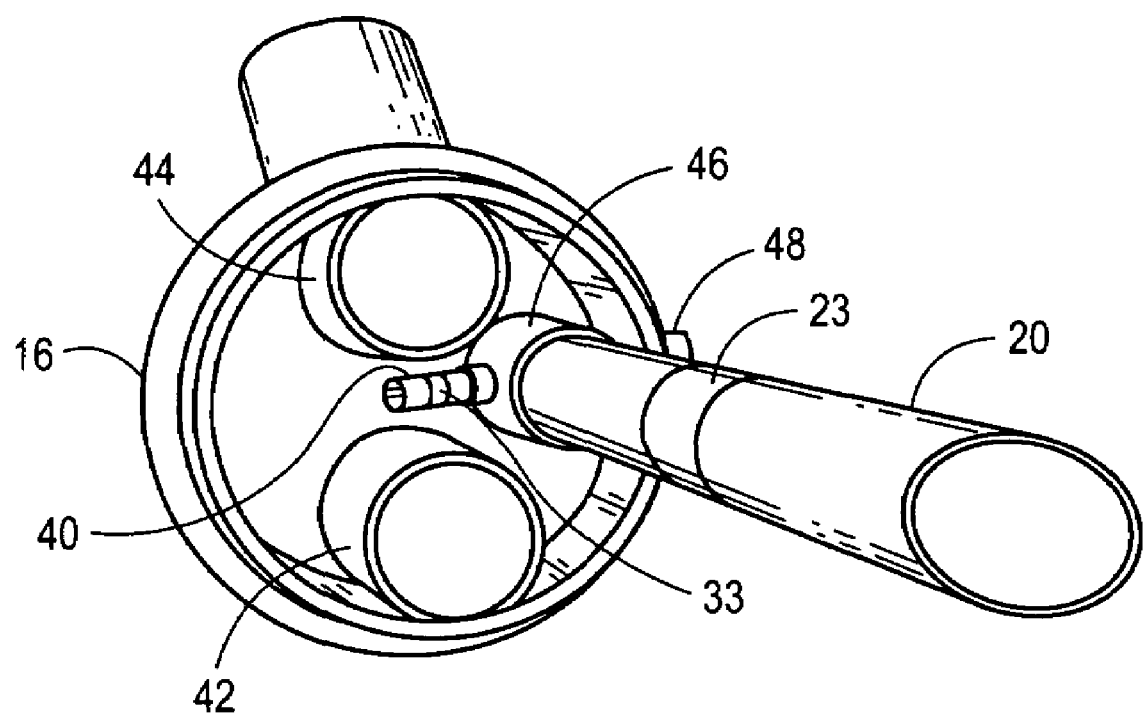
FIG. 4 illustrates a humidifier vessel lid with pressure equalizing components.

FIG. 4 illustrates an example of a lid for a humidifier vessel formed to incorporate the pressure equalizing components of the apparatus described in FIG. 3. On the underside of such a lid illustrated is a respiratory gas inlet extension 44 which communicates with the respiratory gas inlet 14 and a respirator gas outlet extension 42 which communicates with respirator gas outlet 12 shown in FIG. 3. Also present is a pipe adapter 46 for receiving the upper end of water level control pipe 20. A tubing adapter 48 extends from the lid for being secured to tubing 25 shown in FIG. 3. Tubing adapter 48 communicates with a gas pressure vent port formed in the lid and communicating with pipe adapter 46. One-way valve 23 is located in the water level control pipe adjacent to the upper end. However, pipe adapter 46 may be formed so that the one-way valve 23 may be located in the adapter rather than the water level control pipe. The gas pressure vent port pipe 40 extends from the pipe adapter 46 and is formed so as to communicate with pipe adapter 46 above one-way valve 23. Alternatively, the gas pressure vent port pipe 40 and the one-way valve 33 may be positioned in the lid, independent of the pipe adapter 46. If such a location is used, the gas pressure vent port and vent port pipe will be formed in the lid as will be a tubing adapter for communicating the gas pressure vent port with tubing exteriorly of the lid. The lid illustrated in FIG. 4 is a cover for enclosing the upper end of the humidifier vessel 10 as illustrated in U.S. Pat. No. 6,050,522, the description of which is incorporated herein by reference.

Figure 5:
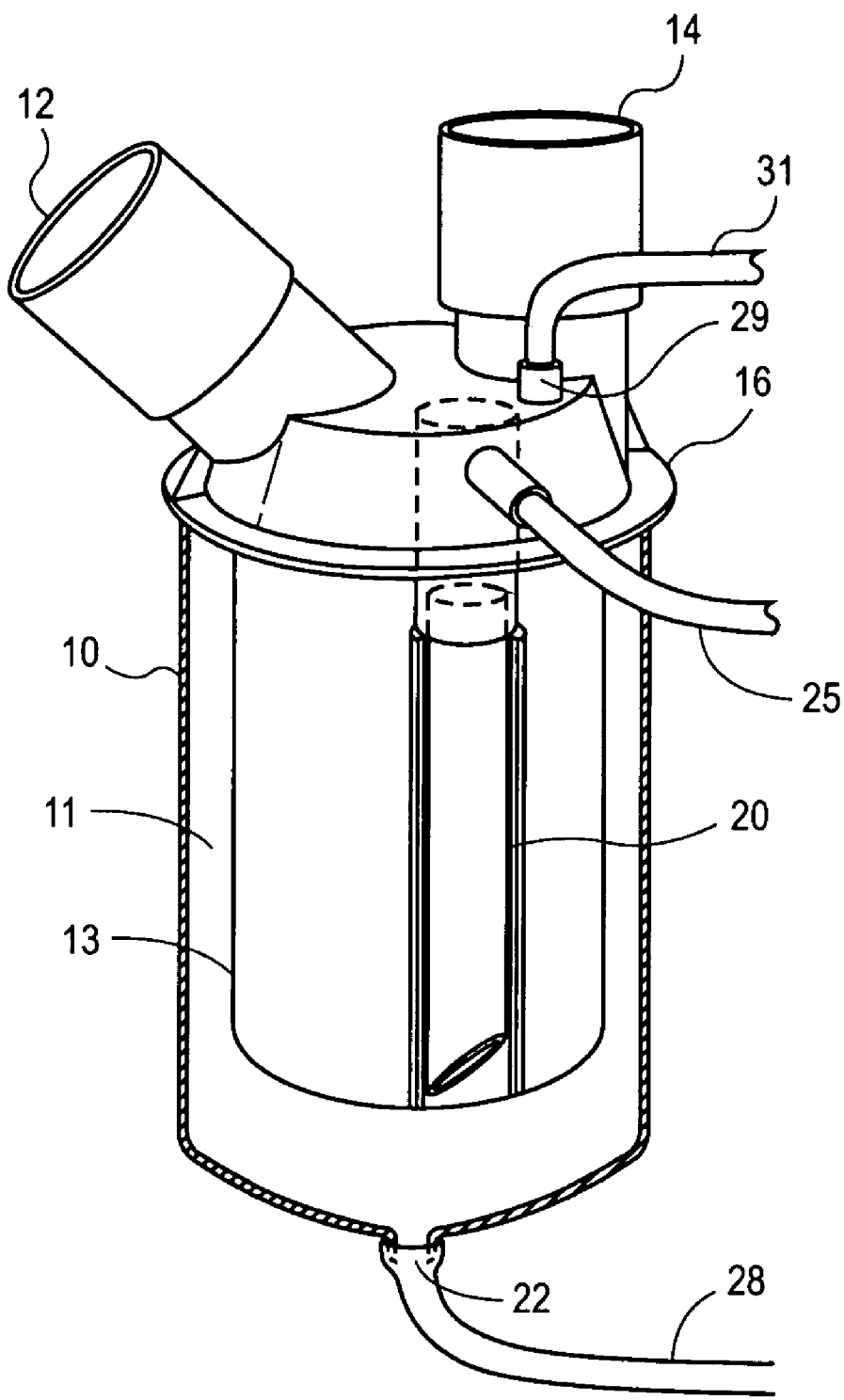
FIG. 5 illustrates a humidifier vessel on which the pressure equalizing tubing is secured and which vessel includes a volume displacement cartridge in the humidification chamber cavity.

FIG. 5 illustrates a humidifier assembly including a volume displacing cartridge 13 within humidifying vessel 10. The cartridge is designed for displacing between a substantial amount, preferably between about 20% and about 80% of the volume of cavity 11 within the humidifying vessel. Other features and components of the preferred embodiment of a volume displacing cartridge are disclosed in U.S. Pat. No. 6,050,552. Features of such a humidifier vessel are as previously described, including the tubing 31 which is secured to adapter 29 on the cap 16 of the humidifying vessel 10.

What is claimed is:

1. A humidifier assembly comprising
   a water supply container enclosing a water containing reservoir;
   a humidifier vessel comprising a water holding cavity having an inlet adjacent to the bottom thereof, a respiratory gas inlet, a respiratory gas outlet, a gas pressure vent port, a water level control port, and a water level control pipe communicating with said water level control port;
   a first one-way valve for directing gas flow through said water level control pipe to said water supply container;
   a second one-way valve for directing gas flow from said water supply container to said gas pressure vent port;
   first piping for directing water from said water supply container to said humidifier vessel;
   second piping cooperating with said first one-way valve and said second one-way valve for equalizing pressure between said water supply container and said humidifier vessel; and wherein said second piping comprises tubing extending between said water supply container and said gas pressure vent port and said water level control port.

2. A humidifier assembly of claim 1 wherein said first one-way valve is located in said water level control pipe.

3. A humidifier assembly of claim 2 wherein said second one-way valve is located in said humidifier vessel between said water level control port and said water holding cavity above water level therein.

4. A humidifier assembly of claim 1 wherein said second one-way valve is located in said humidifier vessel between said water level control port and said water holding cavity above water level therein.

5. A humidifier assembly of claim 1 including a water level control port tubing adapter cooperating with said water level control port and wherein said second piping comprises tubing attached to said water level control port tubing adapter.

6. A humidifier of claim 1 including a third one-way valve cooperating with said first piping for directing flow of water from said water supply container to said humidifier vessel.

7. A humidifier assembly of claim 1 including a cartridge disposed in said water holding cavity, said cartridge having a walled hollow interior isolated from said water holding cavity and wherein said cartridge displaces between about 20% and about 80% of the volume of said water holding cavity.

8. A humidifier vessel for cooperating with a water supply container for providing humidification in a respiratory circuit comprising:
   a humidifier vessel comprising a water holding cavity having an inlet adjacent to a bottom of the water holding cavity, a cover for enclosing an upper end of the humidifier vessel having a respiratory gas inlet, a respiratory gas outlet, a gas pressure vent port, and a water level control port;
   a water level control pipe communicating with said water level control port;
   a first one-way valve for directing gas flow through said water level control pipe to a water supply container;
   a second one-way valve communicating with a tubing for directing gas flow from said water supply container to said humidifier vessel; and said tubing extending between said water supply container and said gas pressure vent port and said water level control port.

9. A humidifier vessel of claim 8 including a cartridge disposed in said water holding cavity, said cartridge having a walled hollow interior isolated from said water holding cavity and wherein said cartridge displaces between about 20% and about 80% of the volume of said water holding cavity.

10. A humidifier assembly comprising:
    a humidifier vessel comprising a water holding cavity having an inlet adjacent to a bottom end of said water holding cavity, a respiratory gas inlet and a respiratory gas outlet each communicating with said water holding cavity adjacent to a top of said water holding cavity, a first port and a generally vertical pipe having an open upper end communicating with said first port and an open lower end for contacting water in said water holding cavity, and a second port communicating with said water holding cavity adjacent to the top of said water holding cavity;
    a water supply container enclosing a water containing reservoir;
    first tubing having one end communicating with said water holding cavity via said inlet and another end communicating with said water containing reservoir adjacent to the bottom thereof, and a first one-way valve cooperating with said first tubing for directing water from said water supply container to said humidifier vessel;
    second tubing having one end communicating with said first port and another end communicating with said water containing reservoir above water level therein, and a second one-way valve cooperating with said second tubing for directing fluid from said pipe to said water containing reservoir; and
    third tubing having a first end communicating with said second port and a second end communicating with said water containing reservoir above water level therein, and a third one-way valve cooperating with said third tubing for directing gas from said water containing reservoir to Said Water holding cavity.

11. A humidifier assembly of claim 10 wherein said humidifier vessel comprises an open top shell forming said water holding cavity and a cap member secured in substantially fluid tight seal to the upper end of said shell and enclosing the open top thereof, and wherein said respiratory gas inlet, respiratory gas outlet, first port and second port are formed in said cap member.

12. A humidifier assembly of claim 11 wherein said second end of said third tubing communicates with said second tubing between said second one-way valve and said water containing chamber.

13. A humidifier assembly of claim 10 wherein said second end of said third tubing communicates with said second tubing between said second one-way valve and said water containing chamber.

14. A humidifier assembly of claim 13 including a tee adapter secured to said second tubing and said third tubing between said second one-way valve and said water containing chamber for communicating said second tubing with said third tubing.

15. A humidifier assembly of claim 10 including a cartridge disposed in said water holding cavity, said cartridge having a walled hollow interior isolated from said water holding cavity and wherein said cartridge displaces between about 20% and about 80% of the volume of said water holding cavity.

* * * * *